United States Patent
Baczkowski

(10) Patent No.: US 6,736,140 B1
(45) Date of Patent: May 18, 2004

(54) EXHALATION EVACUATOR

(75) Inventor: Paul S. Baczkowski, Orchard Park, NY (US)

(73) Assignee: Matrx Medical Inc., Orchard Park, NY (US)

( * ) Notice: Subject to any disclaimer, the term of this patent is extended or adjusted under 35 U.S.C. 154(b) by 0 days.

(21) Appl. No.: 10/388,089

(22) Filed: Mar. 13, 2003

(51) Int. Cl.[7] .............................. A62B 18/02; A62B 23/02
(52) U.S. Cl. ............................. 128/206.21; 128/205.27; 128/910
(58) Field of Search ....................... 128/203.12, 204.12, 128/201.23, 205.25, 205.12, 205.19, 206.12, 206.15, 206.18, 206.21, 206.28, 207.12, 203.29, 910, 911, 207.13, 205.27

(56) References Cited

U.S. PATENT DOCUMENTS

| | | | | |
|---|---|---|---|---|
| 3,799,164 A | * | 3/1974 | Rollins | 128/206 |
| 4,015,598 A | * | 4/1977 | Brown | 128/146.5 |
| 4,151,843 A | * | 5/1979 | Brekke et al. | 128/203 |
| 4,219,020 A | | 8/1980 | Czajka | |
| 4,265,239 A | * | 5/1981 | Fischer, Jr. et al. | 128/205.17 |
| 4,312,339 A | | 1/1982 | Thompson | |
| 4,770,169 A | * | 9/1988 | Schmoegner et al. | 128/207.13 |
| 4,895,172 A | * | 1/1990 | Lindkvist | 128/863 |
| 5,018,519 A | | 5/1991 | Brown | |
| 5,033,464 A | * | 7/1991 | Dlcastilho | 128/205.19 |
| 5,109,839 A | * | 5/1992 | Blasdell et al. | 128/203.12 |
| 5,419,317 A | | 5/1995 | Blasdell et al. | |
| 5,577,693 A | * | 11/1996 | Corn | 248/176.1 |
| 6,135,109 A | * | 10/2000 | Blasdell | 128/206.28 |
| 6,263,874 B1 | * | 7/2001 | LeDez et al. | 128/206.21 |

OTHER PUBLICATIONS

Fraser Sweatman, Inc., The Fraser Scavenger, marketing material, prior to effective filing date.
Fraser Harlake, Instructions Dental Anti–Pollution System, Oct. 1983.
MDS Matrx, A.N.S. Autoclavable Nitrous Scavenger, Oct. 2001.
Matrx, Matrx Single–Use Nasal Hoods, May 2002.

* cited by examiner

Primary Examiner—Aaron J. Lewis
Assistant Examiner—Teena Mitchell
(74) Attorney, Agent, or Firm—Phillips Lytle LLP

(57) ABSTRACT

An improved exhalation evacuator (15) having a mask (16) with an inhalation portion (18) and an exhalation portion (19), a delivery conduit (20) communicating with the mask, a return conduit (21) communicating with the mask, the delivery conduit having a supply end (22) and an inlet end (23), the inlet end having an inlet gas passageway (24) and a first connect port (25), the return conduit having an outlet end (26) and an exhaust end (28), the outlet end having an exhaust gas passageway (29) and a second connect port (30), the gas passageway of the delivery conduit communicating with the inhalation portion, the gas passageway of the return conduit communicating with the exhalation portion, the first connect port engaging the exhalation portion, the second connect port engaging the inhalation portion, the first and second connect ports not having a passageway allowing gas to move between the mask and the delivery and return conduits, respectively, the gas inlet passageway and first connect port having an inverse orientation and functionality with respect to the exhaust gas passageway and the second connect port.

8 Claims, 6 Drawing Sheets

EXHALATION EVACUATOR

TECHNICAL FIELD

The present invention relates generally to the field of devices for administering anesthesia, and more particularly to an improved mask apparatus for administering anesthesia to a patient.

BACKGROUND ART

Apparatus for the administration of anesthetic gas to a patient are known in the prior art. Generally, such apparatus are used by dentists for dispensing anesthetic gases such as oxygen and nitrous oxide to a patient during procedures in the dental office. Such systems generally include a source of the anesthetic gas, an apparatus to deliver the gas to the patient, and a scavenging system whereby the gas that the patient exhales is captured and is prevented from escaping into the room. A mask is fitted to the face of the patient and embraces and covers the nose and/or the mouth of the patient. Flexible tubing between the mask and both the source of the anesthetic gas and the aspirator is employed. Generally, such tubing is in the form of flexible hose. Examples of such apparatus are disclosed in U.S. Pat. Nos. 4,219,020, 4,015,598 and 5,018,519 and shown in FIGS. 3–6.

However, the prior art is problematic. The apparatus known in the prior art have a large number of components and high part count, which increases the costs of manufacturing and assembly. The high number of components also increases the chance of improper assembly when in use. Second, the prior art does not embrace the nose and mouth of a patient as symmetrically and closely as may be desired. Third, the scavenging masks known in the prior art do not fit properly over the head of the patient and are cumbersome because of the number of tubes employed in the delivery and exhaust of the subject gas.

Accordingly, it would be beneficial to have a gas delivery apparatus with an exhalation evacuator which has reduced part count, is balanced, embraces the patient's face appropriately, allows for interchangeable sizes, and generally addresses the deficiencies in the prior art.

DISCLOSURE OF THE INVENTION

With parenthetical reference to the corresponding parts, portions or surfaces of the disclosed embodiment, merely for the purposes of illustration and not by way of limitation, the present invention provides an improved exhalation evacuator (15) having a mask (16) with an inhalation portion (18) and an exhalation portion (19), a delivery conduit (20) communicating with the mask, a return conduit (21) communicating with the mask, the delivery conduit having a supply end (22) and an inlet end (23), the inlet end having an inlet gas passageway (24) and a first connect port (25), the return conduit having an outlet end (26) and an exhaust end (28), the outlet end having an exhaust gas passageway (29) and a second connect port (30), the gas passageway of the delivery conduit communicating with the inhalation portion, the gas passageway of the return conduit communicating with the exhalation portion, the first connect port engaging the exhalation portion, the second connect port engaging the inhalation portion, the first and second connect ports not having a passageway allowing gas to move between the mask and the delivery and return conduits, respectively, the gas inlet passageway and first connect port having an inverse orientation and functionality with respect to the exhaust gas passageway and the second connect port.

The inlet end may have a Y-configuration. The supply end may have a first diameter (31) and the exhaust end may have a second diameter (32) and the first diameter and second diameter may be different diameters. The inlet gas passageway and the first connect port may be integrally molded or permanently affixed to the delivery conduit. The inlet gas passageway and the first connect port may be an integrally molded member detachable from the delivery conduit and the mask. The first connect port may comprise a first cylindrical inner surface (55) that defines a first recess (44) and the second connect port may comprise a second cylindrical inner surface (56) that defines a second recess (33). The second connect port may comprise a bridge member (34) adapted for engagement between the second inner surface and the inhalation portion.

Accordingly, the general object of the present invention is to provide an improved exhalation evacuator.

Another object is to provide an exhalation evacuator which allows for a reduced number of components.

Another object is to provide an exhalation evacuator which reduces the risk of improper assembly.

Another object is to provide an exhalation evacuator which has unique porting on the connecting pieces.

Another object is to provide an exhalation evacuator which is symmetrical and engages the face in a balanced manner.

Another object is to provide an exhalation evacuator which reduces the risk of interchanging the return scavenging tubing and the delivery tubing.

Another object is to provide an exhalation evacuator which reduces the amount of tubing to and from the mask.

These and other objects and advantages will become apparent from the foregoing and ongoing written specification, the drawings and the appended claims.

DESCRIPTION OF THE PREFERRED EMBODIMENTS

Figure 1:
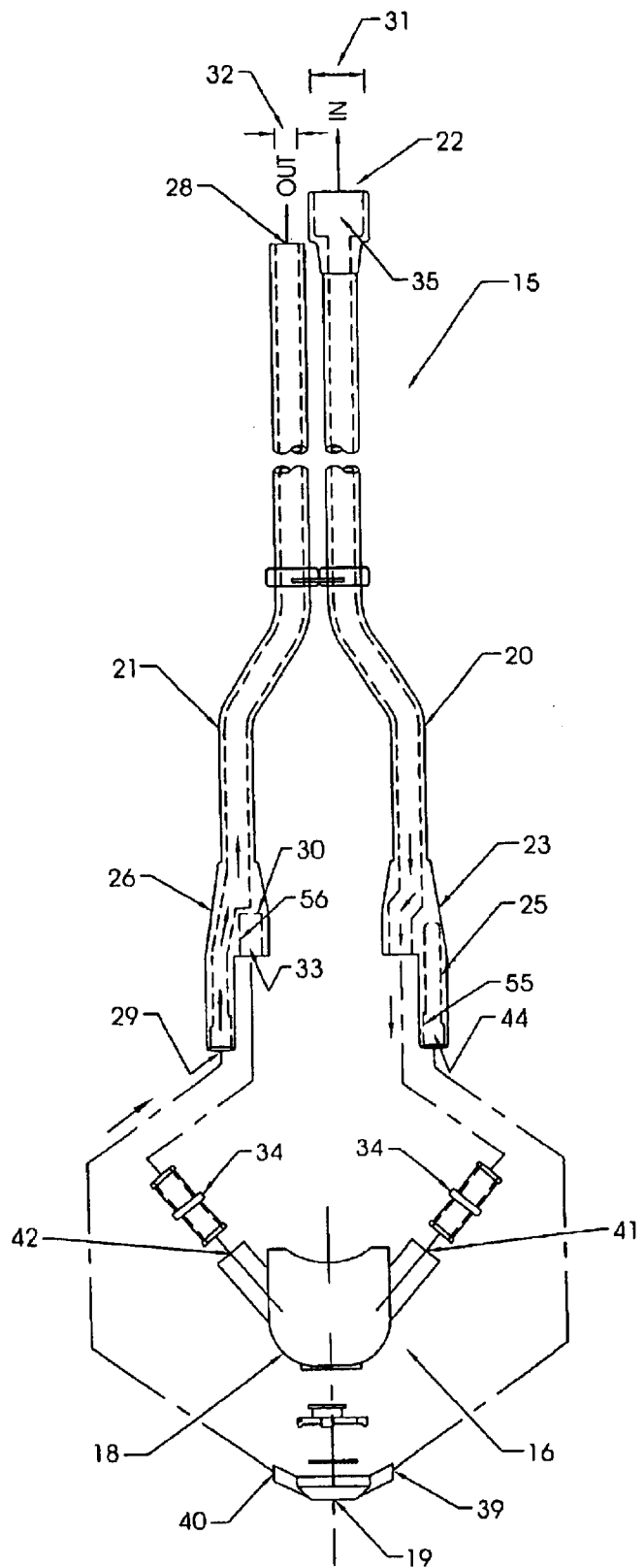
FIG. 1 is an exploded sectional view of the improved exhalation evacuator.

At the outset, it should be clearly understood that like reference numerals are intended to identify the same structural elements, portions or surfaces, consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly"

generally refer to the orientation of a surface relative to its axis of elongation, or axis of rotation, as appropriate.

Figure 2:
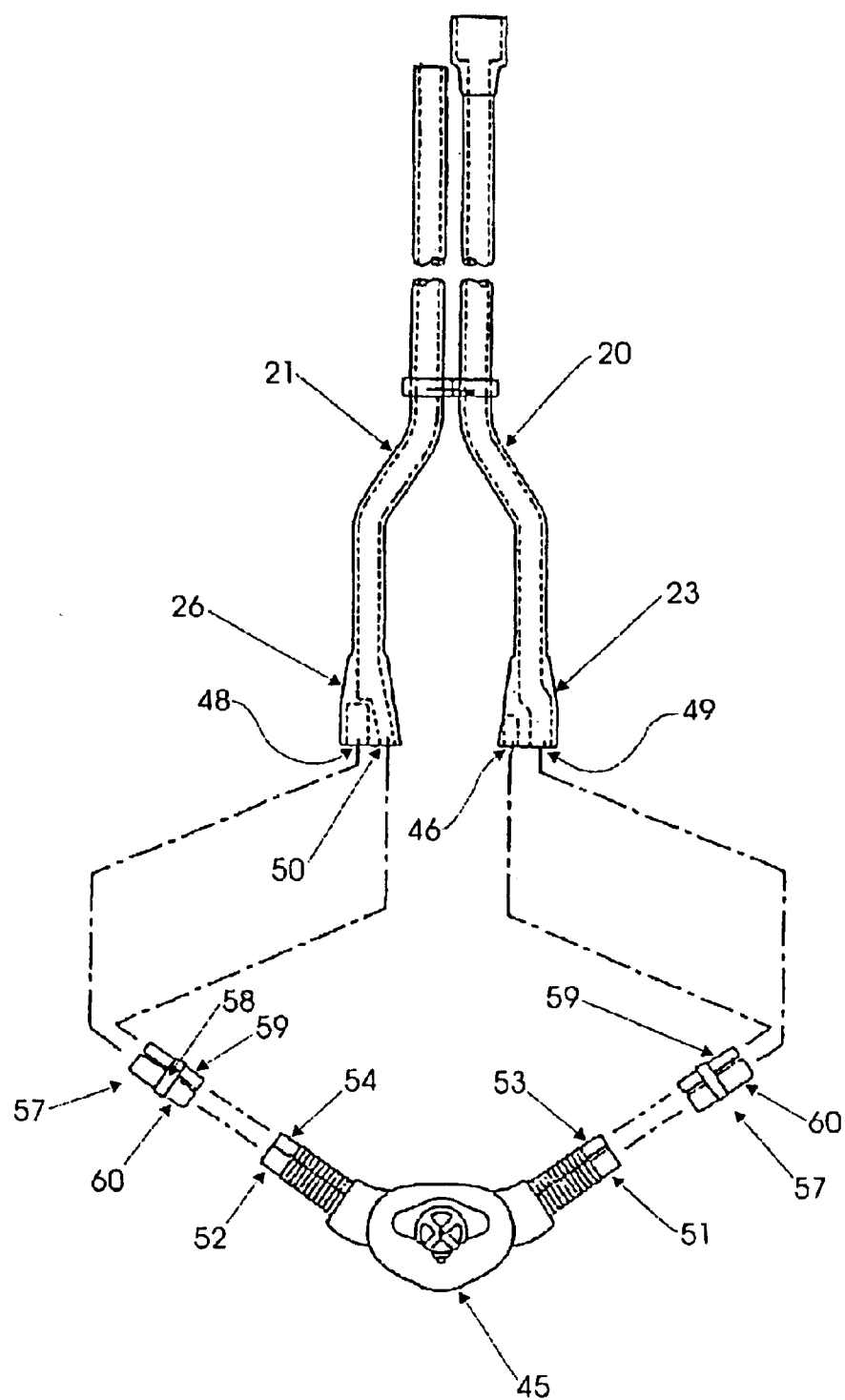
FIG. 2 is a exploded sectional view of a second embodiment of the improved exhalation evacuator as used in connection with an alternate mask.

Referring now to the drawings, and more particularly to FIG. 1 thereof, this invention provides an improved exhalation evacuator, of which the presented preferred embodiment is generally indicated at 15. Exhalation evacuator 15 is shown as broadly including mask 16, delivery tubing 20 and return tubing 21. As shown in FIGS. 1 and 2, delivery tubing 20 has a design which allows it to be connected to a number of different types of masks, including certain masks known in the prior art, such as the mask shown and described in U.S. Pat. No. 5,018,519 and shown in FIG. 2.

As shown in FIG. 1, tubing 20 has a supply end 22 and an inlet end 23. Supply end 22 is adapted for connecting to a source of pressurized gas and includes a supply end port 35 adapted to circumferentially engage the delivery port of the source of pressurized gas (not shown). As used herein, the term port is meant to include either the male or female part of the connection. Port 35 is a cylindrical port which accommodates a properly dimensioned cylindrical supply port. Port 35 has an inside diameter 31, which is slightly smaller and can stretch to fit over the outside diameter of the supply port (not shown), thereby allowing for telescoping engagement of the supply port into port 35.

Delivery tubing 20 also has an inlet end 23. Inlet end 23 includes a cylindrical inlet gas passageway port 24, a cylindrical first connect port 25, and a bridge member 34.

Return tubing 21 is similar to delivery conduit 20, having an exhaust end 28 and an outlet end 26. Exhaust end 28 is adapted to circumferentially engage the vacuum port of the scavenging aspirator (not shown). Exhaust end 28 is cylindrical and has an inside diameter 32. The inside diameter 32 of exhaust end 28 is smaller, in the preferred embodiment, than the inside diameter 31 of supply end 22. By having different diameters to supply end 22 and exhaust end 28, and therefore different diameters on the corresponding ports for the source of pressurized gas and the aspirator, the lines of the evacuator will not be as easily mismatched, thereby reducing the chance that the delivery tubing is improperly attached to the aspirator and the return tubing is improperly attached to the pressurized gas source.

Outlet end 26 of return tubing 21 includes an exhaust gas passageway 29, a connect port 30, and a bridge member 34.

In the embodiment shown in FIG. 1, mask 16 is shown as generally including a hood 18 and a cone 19. In the preferred embodiment, hood 18 is the inhalation portion of mask 16 and cone 19 is the exhalation portion. Hood 18 is a hood generally known in the prior art made of flexible rubber or plastic material molded to fit over the nose bridge of the patient. It is designed for sealing engagement with the facial area of the patient. As shown in FIG. 1, hood 18 includes a first inhalation port 41 and a second inhalation port 42. Cone 19 is a scavenging attachment generally known in the prior art, which acts as a manifold for receiving expired gases and transferring the gases to return tubing 21. Cone 19 includes a first exhalation port 39 and a second exhalation port 40. The Matrx ANS Scavenger mask provided by Matrx of Orchard Park may be used in this embodiment.

Referring now to inlet end 23 of tubing 20, as shown in FIG. 1, the inner cylindrical surface 55 of port 25 defines a first recess 44. First recess 44 is adapted for telescoping circumferential engagement with first exhalation port 39. Interior surface 55 fits tightly over and around the outer cylindrical surface of port 39. Bridge member 34 is designed for telescoping engagement on one end with the inner cylindrical surface of first inhalation port 41 and on the other end with inlet gas passageway 24. Bridge 34 is a hollow cylindrical member.

Outlet end 26 is in a generally inverse symmetrical orientation to inlet end 23. As shown in FIG. 1, second connect port 30 of outlet end 26 includes an inner cylindrical surface 56, which defines a second recess 33. Bridge member 34 is adapted for telescoping engagement on one end with inner surface 56 of port 30 and on the other end with the inner cylindrical surface of port 42. Exhaust gas passageway 29 is adapted to fit tightly over and around the outer cylindrical surface of second exhalation port 40.

As shown in FIG. 1, neither first port 25 nor second port 30 include a passageway to delivery tubing 20 and return tubing 21, respectively. Both first connect port 25 and second connect port 30 are closed-end ports and do not provide a through-passageway. Conversely, inlet gas passageway 24 and exhaust gas passageway 29, as indicated by the arrows shown in FIG. 1, provide a through-passageway between the anesthesia gas supply device and the hood, and the cone and the scavenging aspirator, respectively.

The connecting relationship between the delivery and return tubing 20 and 21 and mask 16 allows for a generally weight-balanced mask when it is placed on the patient's face. Because of this generally weight-balanced relationship, the mask does not tilt relative to a patient's face, thereby providing a tighter fit.

As shown in FIG. 1, inlet gas passageway 24 and first connect port 25 have an inverse orientation and functionality with respect to exhaust gas passageway 29 and second connect port 30. That is: the gas passageway of delivery conduit 20 joins to hood 18, whereas the gas passageway of return conduit 21 joins to cone 19; and the connect port 25 of delivery tubing 20 joins to cone 19, whereas the connect port 30 of return tubing 21 joins to hood 18. This allows not only for the proper circulation of gas, but also for a balanced mask when placed on a patient's face.

FIG. 2 shows an alternate embodiment, in which delivery tubing 20 and return tubing 21 are joined with an alternate mask 45. Similar to the embodiment shown in FIG. 1, inlet end 23 and outlet end 26 each include a gas passageway, 49 and 50 respectively, and a connect port, 46 and 48 respectively. In the embodiment shown in FIG. 2, a bridge member 57 is used to attach connect port 46 and first exhalation port 53, and to connect delivery passage 49 and first inhalation port 51. Likewise, a second bridge 57 is used to attach connect port 48 and second inhalation port 52, and to attach return passageway 50 and second exhalation port 54. Bridges 57 are double barreled hollow cylindrical members connected in parallel by transverse band 58. As shown, the outer circumference of the two barrels 59 and 60 are not the same, with barrel 59 having a smaller outside diameter than barrel 60. One end of barrel 59 fits inside return passageway 50 and the other end fits inside second exhalation port 54. One end of barrel 60 fits inside connect port 48 and the other end fits inside second inhalation port 52. With the other bridge shown in FIG. 2, one end of barrel 60 fits inside delivery passage 49 and the other end fits inside first inhalation port 51, and one end of barrel 59 fits inside connect port 46 and the other end fits inside first exhalation port 53.

In this way, the improved delivery and return tubing may be adapted to be used with conventional scavenging masks known in the prior art. As in the embodiment shown in FIG. 1, the arrangement shown in FIG. 2 allows for the mask to be placed on the patient's face in a balanced manner. The gas travels through delivery tubing 20, out through delivery passage 49, through barrel 60, and in through first inhalation port 51 for delivery to the inhalation portion of hood 45. Exhaled gas travels from the exhalation portion of hood 45, out through second exhalation port 54, through barrel 59, in through return passageway 50, and through return tubing 21 to a conventional scavenging device.

In an alternative embodiment similar to FIG. 2 but not shown, the ports and passageways may be designed such that a bridge member is not included and connect port 46 has an inner cylindrical surface configured to fit tightly over and around the exterior cylindrical surface of first exhalation port 53, the interior cylindrical surface of delivery passage 49 is configured to tightly fit over and around the exterior cylindrical surface of first inhalation port 51, the inner cylindrical surface of connect port 48 is configured to fit tightly over and around the outer cylindrical surface of second inhalation port 52, and the inner cylindrical surface of return passageway 50 is configured to fit tightly over and around the outer cylindrical surface of second exhalation port 54.

The various components of the tubing and bridges can be, alternatively, either integrally molded to each other, permanently affixed, or detachable such that different sized components may be used as desired. Thus, for example, different sized ports and/or bridges may be interchangeably used with tubing 21 and 20 depending on the mask with which the system is used. As used herein, the term integral means molded from a single continuous structure of homogenous material. The term permanently affixed means that adhesive bonds that tubing and molded components.

Figure 3:
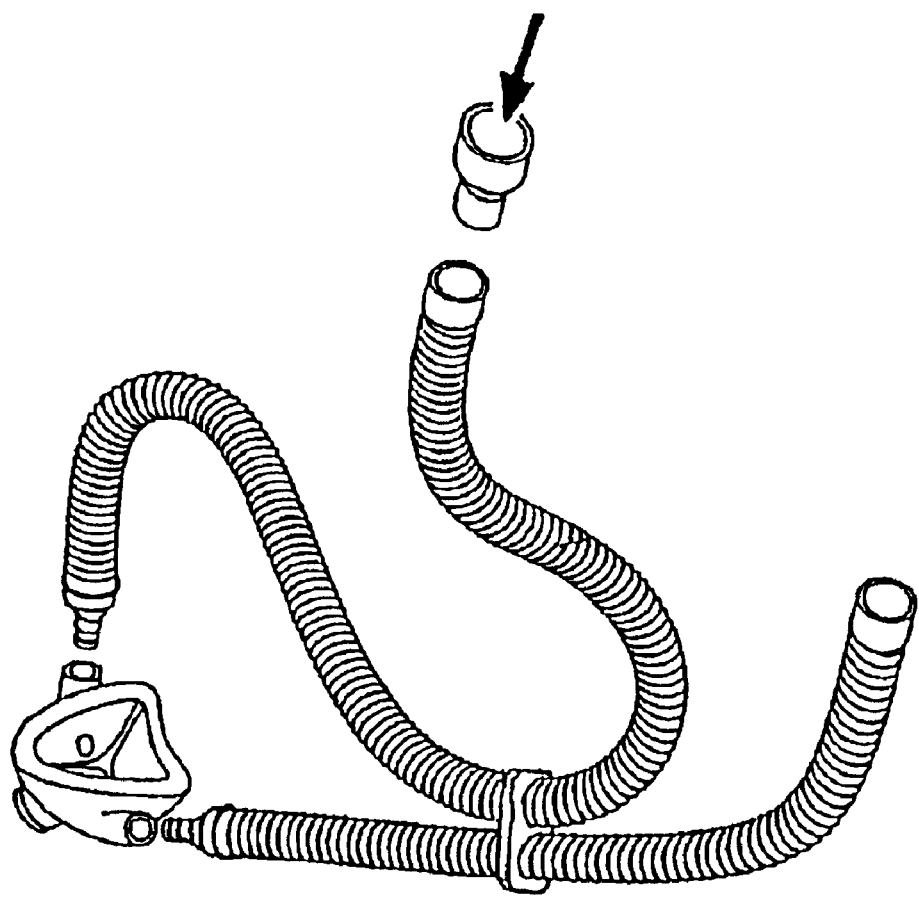
FIG. 3 is an exploded view of an apparatus known in the prior art for administering anesthesia to a patient.

FIG. 3 shows an apparatus known in the prior art and commercialized by Matrx of Orchard Park, N.Y. As shown, this apparatus differs from the present invention in that it does not include a connect port in either the inlet hood end of the delivery conduit nor the outlet hood end of the return conduit.

Figure 4:
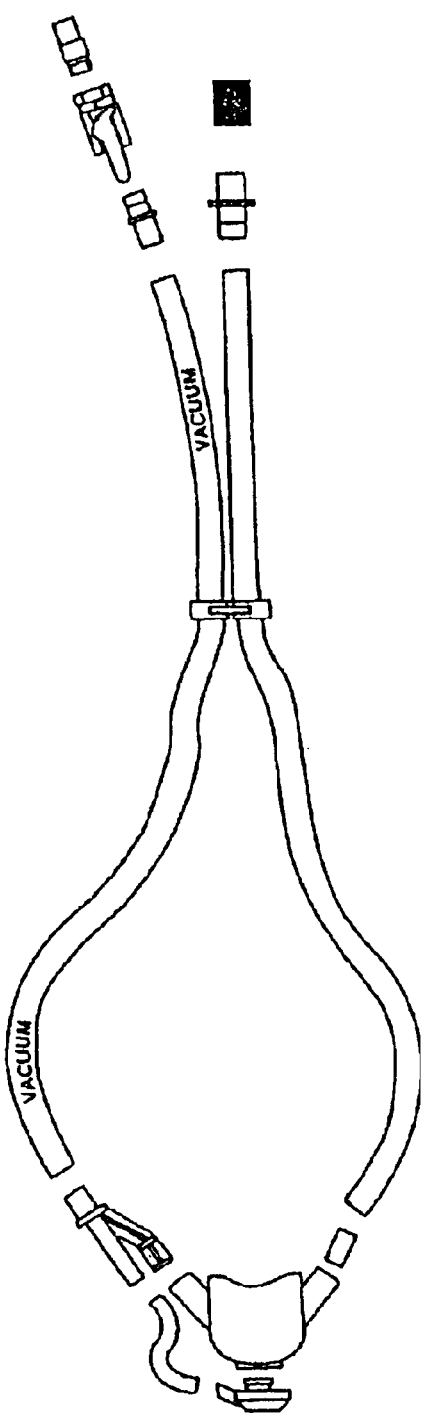
FIG. 4 is a second apparatus known in the prior art for administering anesthesia to a patient.

FIG. 4 shows an alternate apparatus known in the prior art and presently commercialized by Matrx. As shown in FIG. 4, this apparatus differs from the present invention in that the inlet hood end of the delivery conduit does not include a connect port. As shown in FIG. 4, this apparatus thus does not have as balanced a configuration when placed on the patient's face.

Figure 5:
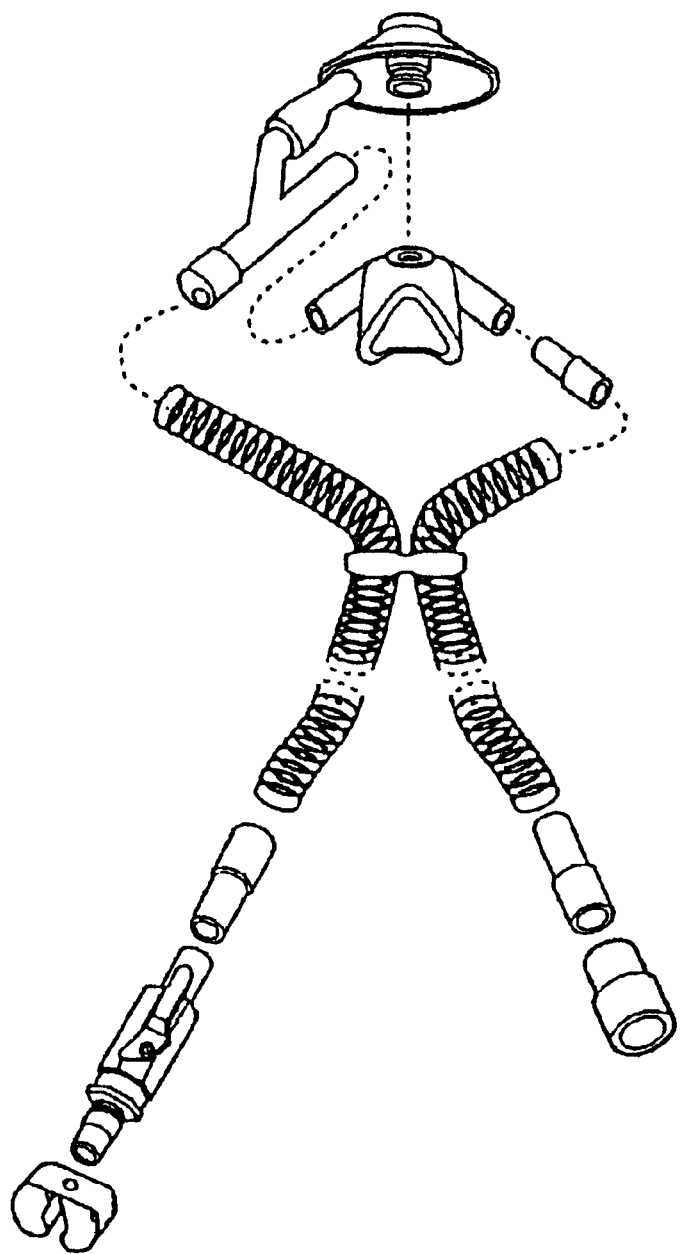
FIG. 5 is a view of a third apparatus known in the prior art for administering anesthesia to a patient.

FIG. 5 shows an apparatus which is the subject of U.S. Pat. No. 4,219,020. Similarly to the apparatus shown in FIG. 3, this apparatus differs from the present invention in that the inlet hood end of the delivery conduit does not include a connect port. Again, one disadvantage of this design is that it does not allow for a balanced fit of the mask on the patient's face.

Figure 6:
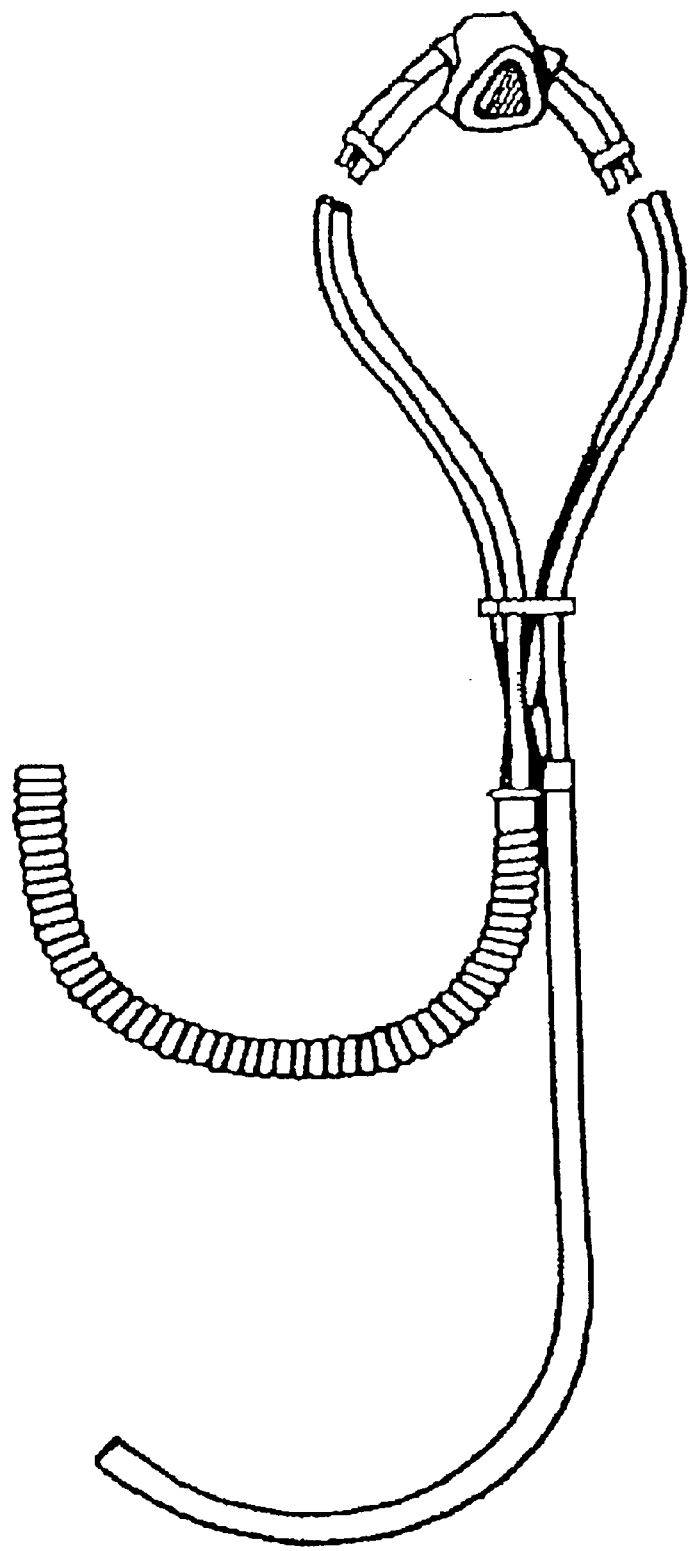
FIG. 6 is an exploded view of a fourth apparatus known in the prior art for administering anesthesia to a patient.

FIG. 6 shows an apparatus known in the prior art and commercialized by Porter Instruments. As shown in FIG. 6, this apparatus has two delivery conduits and two return conduits. The delivery conduits branch off from a central supply conduit and attach to both the left and right hand sides of the mask. Similarly, there are two separate return conduits that branch into a central aspirator conduit and attach to the left and right hand sides of the mask. All four branches from the mask are gas passageways. This apparatus does not have connect ports that are not gas passageways. Because of the multiple supply conduits and multiple return conduits, this apparatus has a higher part count and greater amounts of tubing.

The present invention contemplates that many changes and modifications may be made. The particular materials of which the various body parts and component parts are formed are not deemed critical and may be readily varied. The connect ports may be blocked in the bridge and not at the end of the tubing location as shown. Therefore, while the presently preferred form of the exhalation evacuator has been shown and described, and several modifications discussed, persons skilled in this art will readily appreciate that various additional changes and modification may be made without departing from the spirit of the invention, as defined and differentiated by the following claims.

What is claimed is:

1. An exhalation evacuator comprising:

a mask;

said mask having an inhalation portion and an exhalation portion;

a delivery conduit communicating with said mask;

a return conduit communicating with said mask;

said delivery conduit having a supply end and an inlet end;

said inlet end having an inlet gas passageway and a first connect port;

said return conduit having an outlet end and an exhaust end;

said outlet end having an exhaust gas passageway and a second connect port;

said gas passageway of said delivery conduit communicating with said inhalation portion;

said gas passageway of said return conduit communicating with said exhalation portion;

said first connect port engaging said exhalation portion;

said second connect port engaging said inhalation portion;

said first and second connect ports not having a passageway allowing gas to move between said mask and said delivery and return conduits, respectively;

said inlet gas passageway and said first connect port having an inverse orientation and functionality with respect to said exhaust gas passageway and said second connect port.

2. The exhalation evacuator set forth in claim 1, wherein said inlet end has a Y-configuration.

3. The exhalation evacuator set forth in claim 1, wherein said supply end has a first diameter and said exhaust end has a second diameter and said first diameter and said second diameter are different diameters.

4. The exhalation evacuator set forth in claim 1, wherein said inlet gas passageway and said first connect port are integrally molded to or permanently affixed to said delivery conduit.

5. The exhalation evacuator set forth in claim 1, wherein said inlet gas passageway and said first connect port are an integrally molded member detachable from said delivery conduit and said mask.

6. The exhalation evacuator set forth in claim 1, wherein said first connect port comprises a cylindrical inner surfacing that defines a recess.

7. The exhalation evacuator set forth in claim 1, wherein said second connect port comprises a cylindrical inner surface that defines a recess.

8. The exhalation evacuator set forth in claim 7, wherein said second connect port comprises a bridge member adapted for engagement between said cylindrical inner surface and said inhalation portion.

\* \* \* \* \*